(12) United States Patent
Hong (10) Patent No.: US 10,934,230 B2
(45) Date of Patent: *Mar. 2, 2021

(54) PRODUCTION OF AROMATIC HYDROCARBONS FROM LIGHT ALKANES

(71) Applicant: Kainos Tech Incorporated, Crown Point, IN (US)

(72) Inventor: Jin Ki Hong, Cypress, CA (US)

(73) Assignee: KAINOS TECH INCORPORATED, Crown Point, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,923

(22) Filed: Nov. 27, 2019

(65) Prior Publication Data
US 2020/0094212 A1 Mar. 26, 2020

Related U.S. Application Data

(63) Continuation-in-part of application No. 16/027,432, filed on Jul. 5, 2018, now Pat. No. 10,640,434.

(60) Provisional application No. 62/604,421, filed on Jul. 6, 2017.

(51) Int. Cl.
*C07C 2/76* (2006.01)
*B01J 35/02* (2006.01)
*B01J 8/24* (2006.01)

(52) U.S. Cl.
CPC ................................ *C07C 2/76* (2013.01);
*B01J 8/24* (2013.01); *B01J 35/023* (2013.01)

(58) Field of Classification Search
None
See application file for complete search history.

(56) References Cited

U.S. PATENT DOCUMENTS 10,640,436 B2 * 5/2020 Hong ................ B01J 8/1836
2016/0289141 A1 * 10/2016 Bachmann ............ B01J 8/1872

FOREIGN PATENT DOCUMENTS

GB 1147359 A * 4/1969 ............... C01C 3/20

* cited by examiner

*Primary Examiner* — Philip Y Louie
*Assistant Examiner* — Alyssa L Cepluch
(74) *Attorney, Agent, or Firm* — STIP Law Group, LLC (57) ABSTRACT

Provided is a method for producing aromatic hydrocarbons from light alkanes. A light alkane is contacted with catalyst particles in each of reactors, wherein each of the reactors is a fluidized bed reactor arranged in parallel with each other in a furnace. At least a portion of the alkane feed is converted to aromatic hydrocarbons using the catalyst particles, wherein the aromatic hydrocarbons form a part of a reactor effluent stream. The reactor effluent streams from each of the reactors are merged to form a first merged effluent stream. Catalysts particles deactivated through the light alkane conversion are either regenerated inside the reactors or withdrawn from the reactors for regeneration outside the reactors. The furnace comprises multiple furnaces, and the first merged effluent stream from each of the furnaces is further merged with each other to form a second merged effluent stream.

12 Claims, 6 Drawing Sheets

PRODUCTION OF AROMATIC HYDROCARBONS FROM LIGHT ALKANES

CROSS-REFERENCE TO RELATED APPLICATIONS

This application is a Continuation-In-Part (CIP) of application Ser. No. 16/027,432 filed on Jul. 5, 2018, which in turn claims benefit of Provisional Application No. 62/604,421 filed on Jul. 6, 2017, the disclosures of which are incorporated by reference into the present application.

FIELD OF INVENTION

The present invention relates to a process and an apparatus for producing aromatic hydrocarbons from a light alkane.

BACKGROUND OF THE INVENTION

A stable supply of light alkane feedstock at large volumes enabled by shale gas production incentivizes new chemical process development for key petrochemicals production. Aromatic hydrocarbons are derived from crude oil through catalytic reforming of straight-run heavy naphtha and steam cracking of light naphtha. Driven by geopolitical instabilities in crude oil production regions, production and supply of crude oil has been unpredictable, and its volatile market price has reached unaffordable levels in short period of times. Therefore, a need for cost-advantaged feedstock with a stable supply has been growing for production of aromatic hydrocarbons.

Aromatic hydrocarbons production from light alkanes offers incentives including an abundant and stable supply of feedstock at competitive prices. Light alkanes can undergo catalytic reactions including dehydrogenation, oligomerization, and cyclization in a complex manner until aromatic hydrocarbons are produced. Measurable quantities of hydrogen, methane, light alkanes other than feed alkane, and light alkenes (or light olefins) are also produced as byproducts. Even though light alkanes offer economic incentives as a new feedstock, there remain technical obstacles for industrial scale production of aromatic hydrocarbons from light alkanes.

Light alkane conversion to aromatic hydrocarbons is a strongly endothermic reaction and, therefore, the process for producing aromatic hydrocarbons from light alkanes requires supplying a large quantity of reaction heat. Approximately 4,399 kJ of thermal energy is required for the reaction heat per kg of benzene produced from ethane. The dehydrogenation step of the light alkane feed is mainly responsible for the reaction heat requirement. Considering the strong endothermic requirement, there needs to be a reliable and efficient method and apparatus for providing reaction heat required for producing aromatic hydrocarbons from light alkanes at an industrially attractive production rate.

The present invention found that another important factor in aromatic hydrocarbons production is uniform catalyst bed temperature in a specific temperature range. Findings of the present invention suggest that light alkane conversion for aromatic hydrocarbons production is highly sensitive to reaction temperature in terms of light alkane conversion rate and catalyst deactivation. In case the catalyst bed temperature is below 450° C., light alkane conversion rate is too low to meet commercially attractive production rates. On the other hand, unacceptably fast catalyst deactivation is driven at catalyst bed temperatures higher than 700° C. This fast catalyst deactivation renders a catalyst cycle time between catalyst regenerations too short for commercial operation. Achieving a uniform catalyst bed temperature in a desired temperature range, preferably between 450° C. and 700° C., more preferably between 470° C. and 680° C., and most preferably between 500° C. and 660° C., in industrial scale reactors is critical for commercial viability of aromatic hydrocarbons production from light alkanes.

Methods for supplying reaction heat have been developed by chemical industry for reactions of an endothermic nature. However, adoption of these methods for aromatic hydrocarbons production from light alkane feedstock yields undesirable operational issues and non-uniform temperature distribution in the catalyst bed. For instance, preheating light alkane feedstock to provide sufficient sensible heat for the endothermic reaction is not feasible because the reaction heat required for industrially attractive rates is substantially larger than the quantity of sensible heat achievable through feedstock preheating. Excessive preheating of the feedstock in an attempt to increase sensible heat and provide the reaction heat required often leads to technical issues, including thermal breakdown of feedstock, accelerated catalyst deactivation, and shortened lifetime of preheating tubes. Heating an inter-stage stream for the next stage reactor in a serially connected multi-stage reactors configuration is not practical either because heating of the inter-stage stream leads to thermal breakdown of the desired product at elevated temperatures and its resultant building-up of coke inside the tube.

Intensive heating-up of reactor tubes with a fixed catalyst bed would not be applicable. Catalyst with a fixed position in a stationary state inside an externally heated reactor impedes heat supply itself and creates non-uniform temperature distribution within the catalyst bed. This leads to accelerated catalyst coking and catalyst sintering problems near the reactor wall and not enough thermal energy to drive the endothermic reaction in the center of the catalyst bed.

Catalyst heating by burning coke while regenerating catalyst (and burning extra fuel when needed) and recycling heated catalyst for reaction heat supply has been explored. Even though circulation of heated catalyst particles from the catalyst regenerator for reaction heat supply has been commercially employed in fluid catalytic cracking (FCC) for heavy portions of crude oil, the same approach would not work properly with light alkanes as feedstock. Light alkane conversion for production of aromatics requires substantially larger amounts of reaction heat than cracking of heavy portions of crude oil when compared on a per unit feedstock mass basis. The present invention also found that light alkane feed produces coke at substantially lower yields than FCC for heavy portions of crude oil. The much stronger endothermic requirement of light alkane feed combined with the substantially lower coke yield makes it impractical to use coke as source of reaction heat supply.

Catalyst deactivation driven by coke formation is another technical hurdle in aromatic hydrocarbons production from light alkanes. Formation of coke over or within the catalyst structure progresses over the course of aromatic hydrocarbons production, leading to a gradual drop in aromatic hydrocarbons production rates. Regeneration of deactivated catalysts makes it difficult or impossible to produce aromatic hydrocarbons from a reactor in a continuous manner and to operate downstream separation units without interruption.

Taken together, there is a need for a new process and apparatus for producing aromatic hydrocarbons from a feedstock of light alkanes by developing a reliable and efficient reaction heat supply method to the reactor with uniform catalyst bed temperature in a desired temperature range and by making the entire process continuous.

SUMMARY OF THE INVENTION

A new process and apparatus for producing aromatic hydrocarbons from light alkane feedstock is provided. The process comprises contacting a light alkane feed with catalyst particles in at least two reactors, wherein each of the reactors is a fluidized bed reactor and arranged in parallel with each other in a furnace; converting at least a portion of the alkane feed to aromatic hydrocarbons using the catalyst particles, wherein the aromatic hydrocarbons form a part of a reactor effluent stream; merging the reactor effluent streams from each of the reactors to form a first merged effluent stream. The light alkane may comprise ethane, propane, butane, or a combination thereof. Each of the reactors fluidizes and circulates the catalyst particles inside the reactors. The catalyst particles may be 10-500 micrometers in diameter.

In the converting step, an outside wall of each of the reactors is heated by a flue gas, wherein the flue gas is generated by combustion of a gaseous fuel or a liquid fuel. The pressure of the reactor is 200 prig (1,480 kPa) or less. The temperature of the catalyst particles is between 450° C. and 700° C. during the converting step. The temperature of the furnace is between 700° C. and 1200° C. during the converting step. An end portion of each of the reactors is protruded from the furnace ceiling, wherein the protruded portion is 10%-70% of the length of each of the reactors in a height direction.

The process may further comprise a step of regenerating the catalyst particles by either an internal-regeneration mode or an external-replacement mode, wherein the internal-regeneration mode regenerates the catalyst particles deactivated during the converting step inside the reactors and the external-replacement mode withdraws the deactivated catalyst particles from the reactors for catalyst regeneration outside the reactors and introduces catalyst particles that have sufficient activity into the reactors to resume aromatic hydrocarbons production.

In one embodiment, the furnace comprises multiple furnaces, and the first merged effluent stream from each of the furnaces is further merged with each other to form a second merged effluent stream. The reactors in the furnace in which the catalyst regenerating step occurs may be fluidly disconnected from the second merged effluent stream.

DETAILED DESCRIPTION OF THE INVENTION

Figure 1:
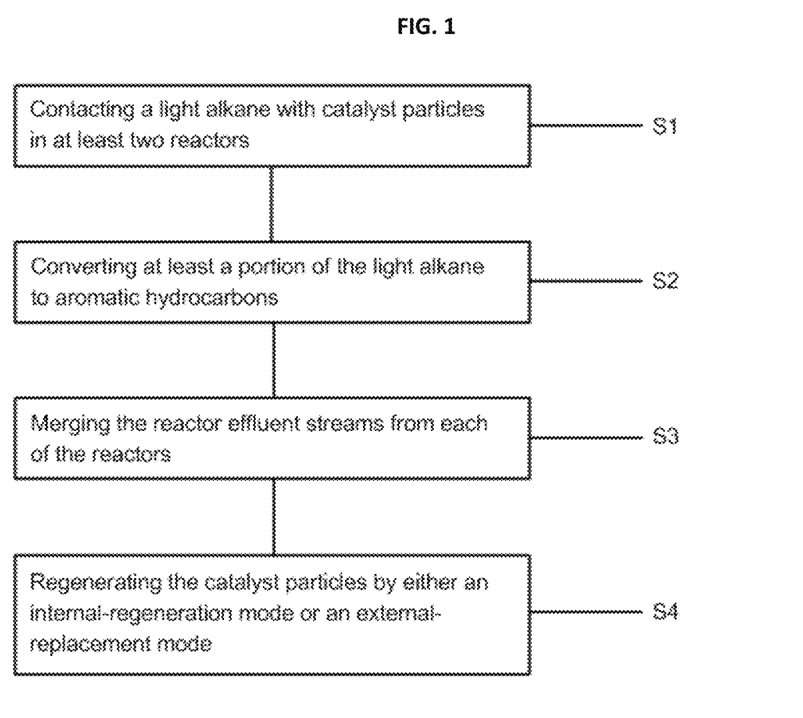
FIG. 1 shows the steps of producing aromatic hydrocarbons from a light alkane feed.

FIG. 1 shows a process for producing aromatic hydrocarbons which comprises contacting a light alkane with catalyst particles in at least two reactors (S1), converting at least a portion of the alkane to aromatic hydrocarbons (S2), merging reactor effluent streams from each of the reactors (S3), and regenerating the catalyst particles by either an internal-regeneration mode or an external-replacement mode, wherein the internal-regeneration mode regenerates the catalyst particles deactivated during the converting step inside the reactors and the external-replacement mode withdraws the deactivated catalyst particles from the reactors for catalyst regeneration outside the reactors and introduces catalyst particles that have sufficient activity into the reactors to resume aromatic hydrocarbons production (S4).

The light alkane comprises ethane, propane, butane or any combination thereof. Light alkane is also referred to as lower alkane or light or lower paraffin. The aromatic hydrocarbons comprise benzene, toluene, and xylene isomers.

Figure 2A:
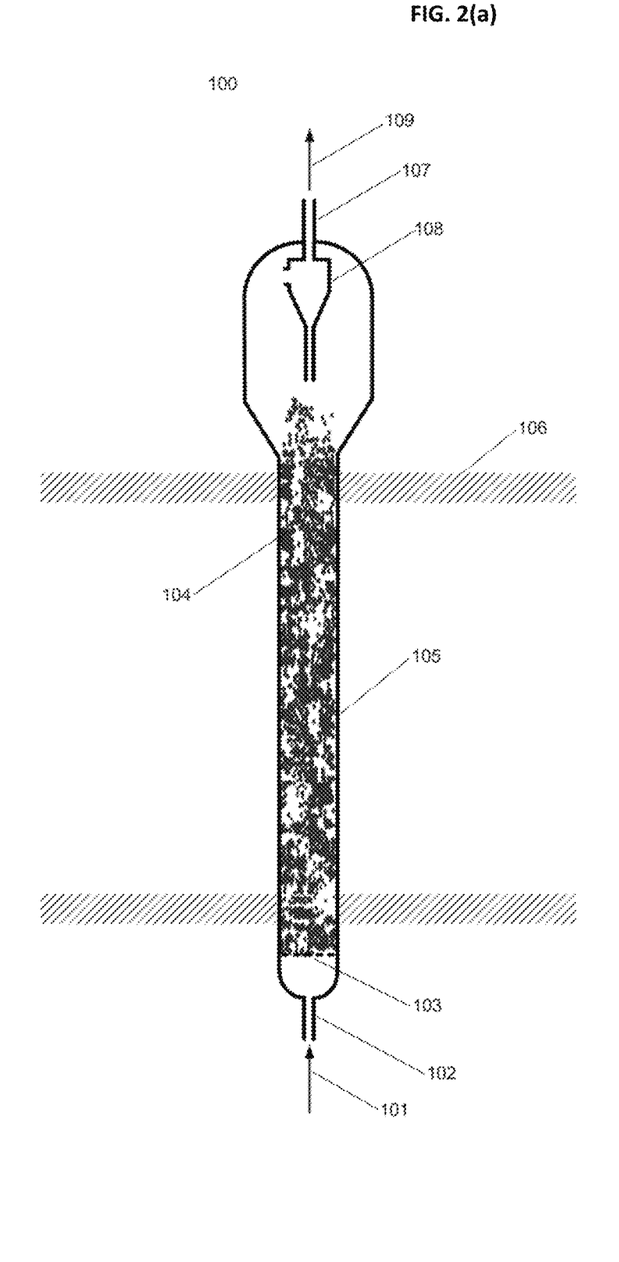
FIGS. 2(a) and 2(b) are simplified schematic diagrams of a fluidized bed reactor of the present invention, where the catalyst regenerating step occurs by an internal-regeneration mode in FIG. 2(a) and by an external replacement-mode in FIG. 2(b), respectively.

FIG. 2(a) shows a simplified schematic diagram of a fluidized bed reactor (cross-sectional view) of the present invention, where the catalyst regenerating step occurs by an internal-regeneration mode.

Reactor feed 101 enters a fluidized bed reactor 100 through reactor feed inlet 102. Fluidization plate 103 promotes fluidization of catalyst particles (or catalyst bed) 104. The catalyst particles comprise bi-functional catalysts and a binder material. The bi-functional catalyst further comprises a dehydrogenation catalyst and an acid catalyst. The dehydrogenation catalyst further comprises a noble metal or a non-noble metal or a combination thereof. The acid catalyst comprises a zeolite material with acidity and controlled pore size. Examples include ZSM-5, ZSM-11, ZSM-23, ZSM-35 and ZSM-48. The binder material holds individual catalyst powders together to make a spherical shape of controlled particle sizes, and improves mechanical strength or attrition resistance of the catalyst particles. The binder is thoroughly mixed with metal-loaded zeolite powder before being transferred to spray drying or other mechanical operation for particles formation. The finished catalyst particles are 10-500 micrometers (or microns) in diameter. Fluidization plate 103 may take the form of porous metal plate/disk, bubble cap plates, or spargers. The gas flow rate is regulated for fluidization regimes of either bubbling or turbulent fluidization, or in between the two. Flow rates lower than dense bed transition velocity or higher than transport velocity is not desirable for the present invention.

Thermal energy is transferred from the hot flue gas to the catalyst particles (or catalyst bed) 104 and the gas flow inside the reactor 100 through reactor wall 105 during the light alkane converting step. The fluidized bed reactor may be partially embedded in a furnace where the hot flue gas from combustion of gaseous or liquid fuel provides thermal energy through the reactor wall to the catalyst particles and gas flow inside the reactor.

An upper end portion of the reactor is protruded from furnace ceiling 106, wherein the protruded portion is 10%-70% of the length of the reactors in a height direction. The length of the reactor is defined as the length between the uppermost of reactor feed inlet 102 and the lowermost of reactor effluent outlet 107. A lower end portion of the reactor may be protruded from a furnace floor when it is needed to avoid excessively high temperature around fluidization plate 103 by hot flue gas.

Catalyst particles (or bed) 104 need to reach at least the height of or the level of inner wall of furnace ceiling 106 during the light alkane converting step. In case the fluidized catalyst particles do not reach the level of furnace ceiling inner wall and, therefore, stay below the level of furnace ceiling inner wall, then the reactor space above the catalyst particles and below the level of furnace ceiling inner wall does not have catalyst particles that can drive endothermic reaction. As heat supplied through the reactor wall surrounding the empty reactor space below the level of furnace ceiling inner wall is not consumed, the reactor wall portion becomes overheated. This overheated reactor wall portion accelerates thermal breakdown of hydrocarbons including desired products, leading to gradual build-up of coke layer over the overheated reactor wall portion.

The overheated reactor wall portion is also a critical problem as it shortens the lifetime of the reactor. Elevated temperature drives deformation and, as a result, shortens the lifetime of the metal through creep failure or creep rupture. As has been demonstrated by the Larson-Miller curves for high temperature alloys, the lifetime of the reactor under stress is shortened as a result of the overheated reactor wall portion. Temperature elevation as small as 30° C. or higher has a significant impact on the lifetime of the metal.

The protrusion of the reactor from the furnace ceiling 106 provides space so that catalyst particles under fluidization can reach at least the level of furnace ceiling inner wall inside the reactor. The reactor space above the level of furnace ceiling serves as freeboard or catalyst disengagement section.

Cyclone with dipleg 108 separates catalyst fines or particles from gas stream leaving the reactor and returns them to the reactor 100. This minimizes or avoids entrainment of the catalyst fines or particles out of the reactor 100. Multiple cyclones may be connected in series for improved separation of catalyst fines or particles. The cyclone or cyclones may be installed either internally or externally to the reactor. Reactor effluent 109 leaves the reactor 100 through reactor effluent outlet 107.

Upward flow of the light alkane feed inside the reactor drives fluidization of the catalyst particles and promotes heat transfer from inner surface of the reactor wall to the catalyst particles and gas flow inside the reactor. Driven by the fluid-like behavior of the catalyst particles, heat transfer coefficient as high as 600 W/m$^2$-K is readily achievable compared to less than 100 W/m$^2$-K in non-fluidized heat transfer cases. The high thermal mass or heat capacity of the catalyst particles impinging the inner wall of the fluidized bed reactor at a high frequency substantially improves heat transfer to the catalyst particles and gas flow inside the reactor. Uniform catalyst bed temperature is realized, which is attributable to large surface area of catalyst particles circulating within the reactor that are in contact with surrounding gas flow.

Traditional heat supply through a fixed catalyst bed is highly limited as the catalyst in stationary position itself impedes heat transfer. As a result, steep temperature gradients develop across the catalyst bed. Excessively hot catalysts near the reactor wall are susceptible to catalyst deactivation and thermal degradation while catalysts located away from the reactor wall lack thermal energy and are unable to drive endothermic reactions.

FCC-type heat supply through coke burning in deactivated catalyst particles and circulation of the heated catalyst particles is not suitable for light alkane conversion because coke yield in light alkane conversion is too low to meet the reaction heat required for industrially attractive production rates. Light alkane dehydrogenation for aromatic hydrocarbons production requires much larger reaction heat than scission of carbon-carbon bond in cracking of heavy portions of crude oil in an externally circulating fluidization system. Compared to 5 mole % or higher coke yield obtainable in catalytic cracking of heavy portions of crude oil in an externally circulating fluidization system, light alkane conversion to aromatic hydrocarbons produces less than 1 mole % of coke yield. This low yield of coke cannot provide sufficient reaction heat through coke burning for industrially attractive conversion rates in an externally circulating fluidization system. Burning additional fuel in order to raise catalyst particles temperature would lead to an undesirable increase of heavy aromatics production and loss in catalyst performance and mechanical strength of the catalyst.

The reactor wall material of the present invention is comprised of alloy metals that exhibit high thermal conductivity. Thermal conductivities higher than 20 W/m-K of the alloy metals have proven effective for heat transfer in high temperature chemical processes such as steam crackers for olefins production and steam methane reformers for synthesis gas production. Heat flux higher than 40 kW/m$^2$ is achievable through the reactor wall made of the alloy metals.

Catalyst bed temperatures are preferably maintained between 450° C. and 700° C., more preferably between 470° C. and 680° C., and most preferably between 500° C. and 660° C. during the light alkane converting step. Above 700° C., catalyst deactivation driven by coking progresses rapidly and shortens the cycle time between catalyst regenerations. Below 450° C., the light alkane conversion rate is too low to meet industrially attractive conversion rates. The reactor pressure is 200 psig (1,480 kPa) or less, preferably between 30 psig (308 kPa) and 90 psig (722 kPa).

When the light alkane conversion drops below a predetermined conversion rate by catalyst deactivation, the catalyst particles are regenerated by the internal-regeneration mode. In catalyst regeneration by the internal-regeneration mode, the reactor is purged with inert gas such as nitrogen to remove hydrocarbons in the reactor. Subsequently, the reactor is fed with air, diluted air or hydrogen to either oxidize the coke or convert the coke to methane and recover the activity of the catalyst particles. The coke burn-off or coke conversion to methane occurs under controlled catalyst bed temperature in order to avoid irreversible damage to the catalyst particles by excessively high temperatures. When the coke burn-off or coke conversion to methane is completed, then the reactor is purged with inert gas to remove oxygen inside the reactor and fed with light alkane to transition to the light alkane converting step. The catalyst regenerating step by the internal-regeneration mode may be understood as in-situ catalyst regeneration.

Figure 2B:
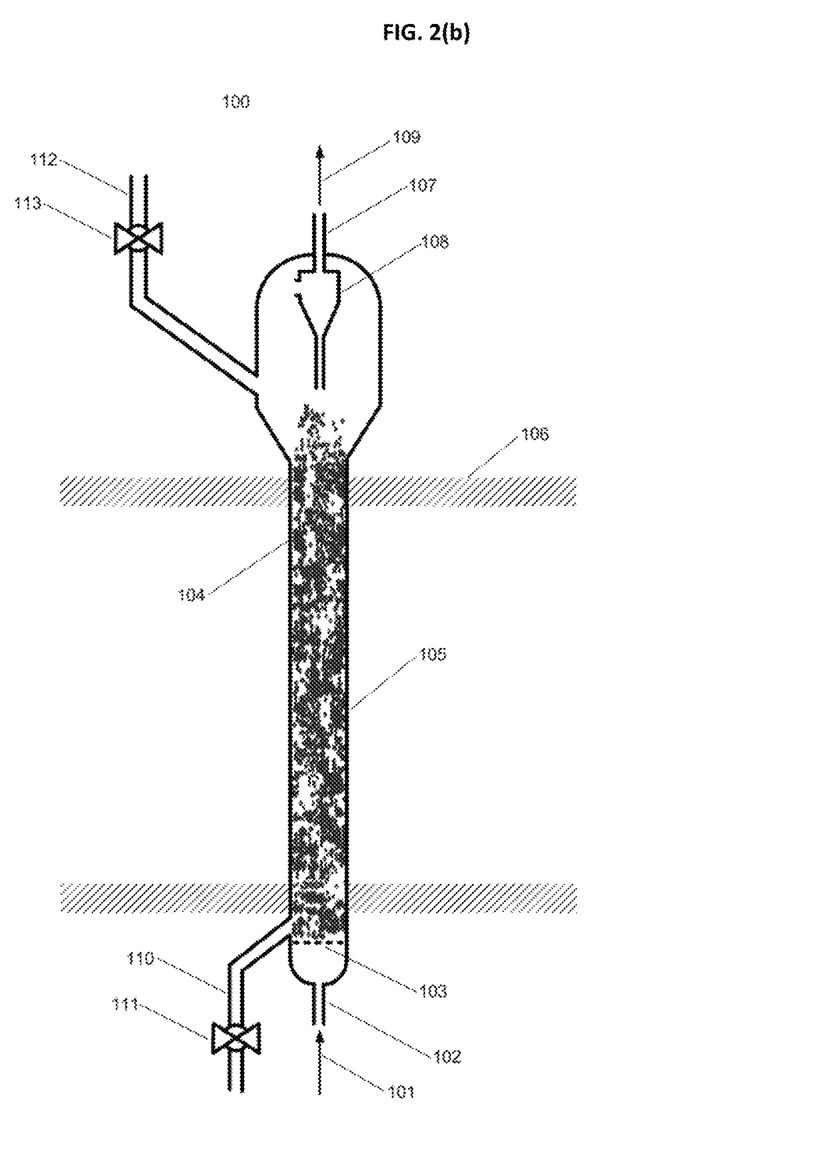

FIG. 2(b) shows a simplified schematic diagram of a fluidized bed reactor (cross-sectional view) of the present invention, where the catalyst regenerating step occurs by an external-replacement mode. In catalyst regenerating step by the external-replacement mode, deactivated catalyst particles are withdrawn from the reactor and catalyst particles that have sufficient catalytic activity are introduced to the reactor. In order to accommodate withdrawal of deactivated catalyst particles out of the reactor and introduction of catalyst particles that have sufficient activity into the reactor, the reactor in FIG. 2(b) has additional parts or features such as catalyst withdrawal passage 110, catalyst withdrawal valve 111, catalyst introduction passage 112, and catalyst introduction valve 113. When the light alkane conversion drops below the predetermined conversion rate by catalyst deactivation, the reactor is purged with inert gas such as nitrogen to remove hydrocarbons in the reactor. Subsequently, the catalyst bed temperature is dropped to an acceptable level and the catalyst particles are withdrawn from the reactor through catalyst withdrawal passage 110 and catalyst withdrawal valve 111. Catalyst particles of reduced activity or deactivated catalyst particles, after withdrawal from the reactor, are processed in a designated facility to recover its catalytic activity. The recovery or regeneration process in a designated facility may include coke burn-off and optional re-dispersion of noble metal such as Pt. Coke burn-off is performed using air or diluted air under controlled catalyst bed temperature. For re-dispersion of agglomerated noble metal, catalyst particles are treated with chlorine-containing gas. Catalyst particles with sufficient activity, either fresh or regenerated catalyst particles, are introduced to the reactor through catalyst introduction passage 112 and catalyst introduction valve 113. The catalyst regenerating step by the external-replacement mode may be understood as ex-situ catalyst regeneration. The withdrawal or introduction of catalyst particles may be performed by mechanical operations such as gravity force, entrainment, conveyor, and suction.

Figure 3A:
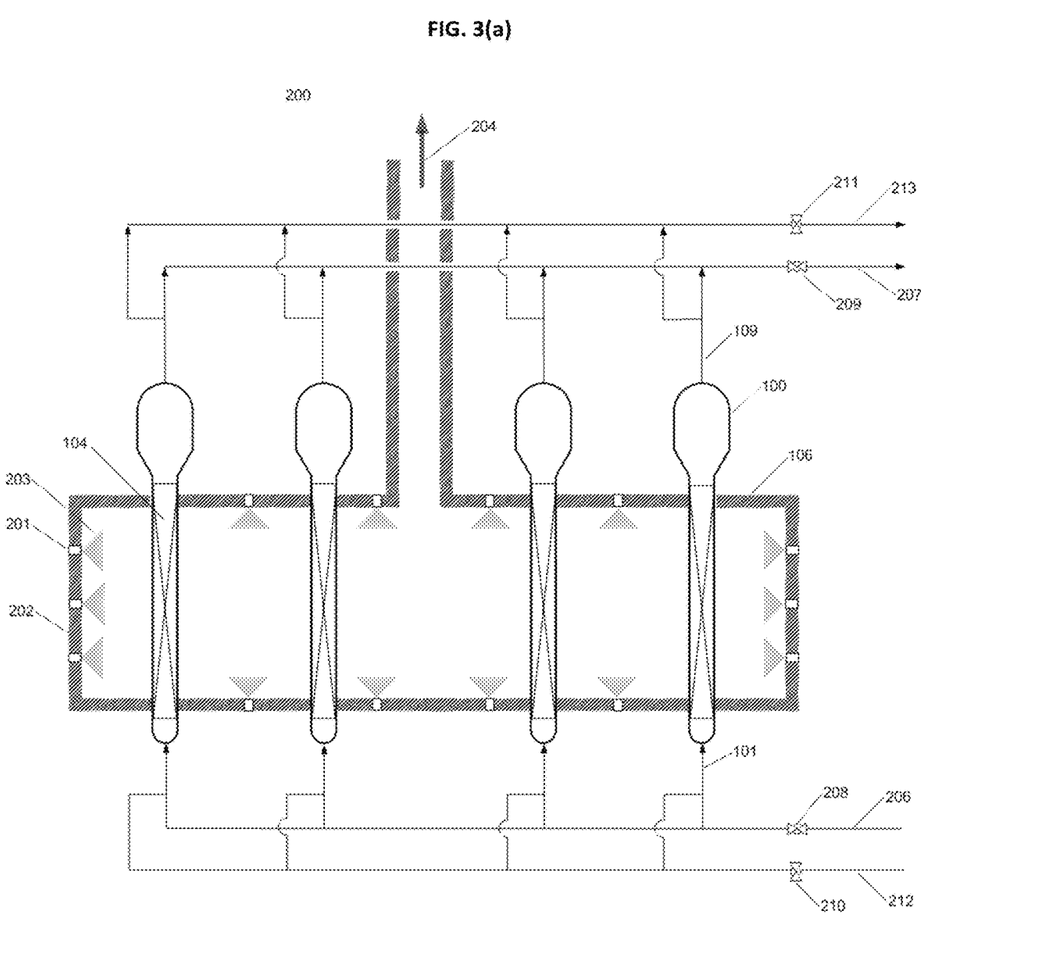
FIGS. 3(a) and 3(b) are simplified schematic diagrams of a furnace of the present invention in which multiple fluidized bed reactors are arranged in parallel and the reactors are heated by flue gas during the light alkane conversion step. The catalyst regenerating step occurs by an internal-regeneration mode in FIG. 3(a) and by an external-replacement mode in FIG. 3(b), respectively.

FIG. 3(a) shows a simplified schematic diagram of furnace 200 of the present invention in which multiple reactors 100 are heated by flue gas during the light alkane converting step and the catalyst regenerating step occurs by the internal-regeneration mode (i.e., in-situ catalyst regeneration). The reactors are fluidized bed reactors. The reactors are arranged in parallel with each other in furnace 200. The number of reactors varies depending on target production rate and production rates of individual reactors.

An upper end portion of each of the reactors may be protruded from furnace ceiling 106, wherein the protruded portion may be 10%-70% of the length of each of the reactors in a height direction. On an inner wall area including a floor or a ceiling of the furnace, multiple burners 201 are installed, and the burners produce flue gas 203 by combusting gaseous or liquid fuel. Burners 201 are positioned in such a way that promotes uniform distribution of thermal energy by the flue gas flow inside the furnace and avoids formation of hot spots on the reactor wall. A lower end portion of the reactor may be protruded from furnace floor when it is needed to avoid excessively high temperature around the fluidization plate by hot flue gas.

Catalyst particles (or bed) 104 need to reach at least the height or the level of inner wall of furnace ceiling 106 during the light alkane converting step. In case the fluidized catalyst particles do not reach the level of furnace ceiling inner wall and, therefore, stay below the level of furnace ceiling inner wall, then the reactor space above the catalyst particles and below the level of furnace ceiling inner wall does not have catalyst particles that can drive endothermic reaction. As heat supplied through the reactor wall surrounding the empty reactor space below the level of furnace ceiling inner wall is not consumed, the reactor wall portion becomes overheated. This overheated reactor wall portion accelerates thermal breakdown of hydrocarbons including desired products, leading to gradual build-up of coke layer over the overheated reactor wall portion.

Light alkane feed 206, which is introduced by opening light alkane feed valve 208, is split into multiple streams which are fed into individual reactors 100. Reactor effluents 109 from each of the reactors are merged to form first merged effluent stream 207 by opening first merged effluent valve 209. The furnace temperature or flue gas temperature inside the furnace is preferably between 700° C. and 1200° C., more preferably between 750° C. and 1150° C., and most preferably between 800° C. and 1100° C., providing temperature gradients high enough for heat supply needed for the industrially attractive light alkane conversion rates. Flue gas flowing around outer walls of the reactors provides thermal energy to the reactors through radiation and convection mechanism. The rate of heat transfer from hot flue gas is high enough to convert the light alkane at industrially attractive rates. Flue gas leaving the furnace 204 may provide thermal energy for preheating light alkane feed 206 or other heating duties in order to improve efficiency of the process.

The fluidized bed reactors in a furnace may be transitioned as a group between the light alkane converting step and the catalyst regenerating step. The catalyst regenerating step occurs by the internal-regeneration mode. The reactors are transitioned to the catalyst regenerating step as a group when the light alkane conversion rate drops below the predetermined rate. Light alkane feed valve 208 and first merged effluent valve 209 are closed when transitioning to the catalyst regenerating step. Subsequently, regeneration gas feed valve 210 and regeneration effluent valve 211 are opened to introduce regeneration gas feed 212 and to withdraw merged regeneration effluent 213, respectively. Depending on the status of reactor operation, regeneration gas feed 212 introduces gases such as nitrogen for reactor purging, air or diluted air for coke burn-off, or hydrogen gas for coke conversion to methane.

It is not desirable to have one group of reactors in the light alkane converting step, while the other group of reactors in the catalyst regenerating step concurrently in the same fired furnace. Catalyst regeneration, such as coke burning using air or coke gasification to methane using hydrogen, is a strong exothermic reaction. In case the exothermic catalyst regenerating step by the internal-regeneration mode is performed in some reactors, while other reactors are in the light alkane converting step concurrently in a fired furnace, then the temperature of catalyst particles inside the reactors of catalyst regenerating step elevates to an unacceptably high level. This leads to thermal degradation of catalyst particles including catalyst sintering and catalytic performance loss.

When the coke burn-off or coke conversion to methane is completed, the reactors are fed with light alkane to transition to the light alkane converting step. The reactors may be purged with inert gas such as nitrogen before and after the catalyst regenerating step. The reactor purge may be needed to prevent uncontrolled or accidental reaction of residual hydrocarbon gases with oxygen.

Figure 3B:
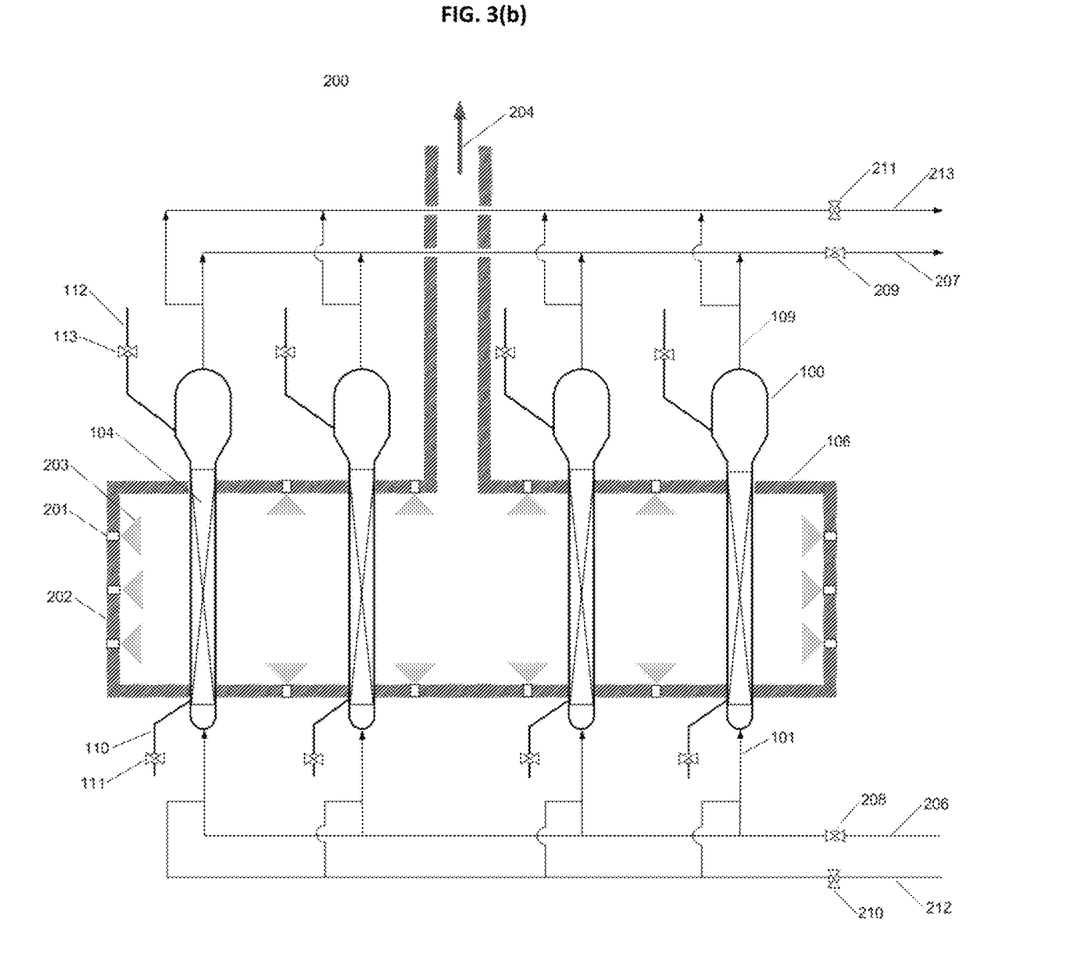

FIG. 3(b) shows a simplified schematic diagram of furnace 200 of the present invention in which multiple reactors 100 are heated by flue gas during the light alkane converting step and the catalyst regenerating step occurs by the external-replacement mode. In the catalyst regenerating step by the external-replacement mode, catalyst particles of reduced activity are withdrawn from each of the reactors as a group for catalyst regeneration outside the reactors. Before withdrawing the catalyst particles, flue gas production in the furnace is stopped in order to drop the furnace temperature and catalyst bed temperature in the reactors. Each of the reactors is purged with inert gas to remove residual hydrocarbons. Purging of the reactors is performed through proper operation of light alkane feed valve 208, first merged effluent valve 209, regeneration gas feed valve 210, and regeneration effluent valve 211. The purge gas is supplied from regeneration gas feed 212 and the purge gas out of the reactors is merged with each other to form merged regeneration effluent 213.

Deactivated catalyst particles are withdrawn from each of the reactors through catalyst withdrawal passage 110 and catalyst withdrawal valve 111. After the withdrawal, catalyst particles that possess sufficient catalytic activity are introduced to each of the reactors through catalyst introduction passage 112 and catalyst introduction valve 113.

The fluidized bed reactors in the furnace may be transitioned as a group between the light alkane converting step and the catalyst regenerating step. The catalyst regenerating step is performed by the external-replacement mode. It is not desirable to have one group of reactors in the light alkane converting step, while the other group of reactors in the catalyst regenerating step concurrently in the same fired furnace. There is no endothermic reaction occurring in the reactors undergoing the catalyst regenerating step by the external-replacement mode. In case the catalyst particles are being withdrawn or introduced in some reactors, while other reactors are in the light alkane converting step concurrently in the same fired furnace, then the temperature of catalyst particles in reactors undergoing the catalyst regenerating step may reach unacceptably high level. This leads to thermal degradation of catalyst particles including catalyst sintering and catalyst performance loss.

Figure 4:
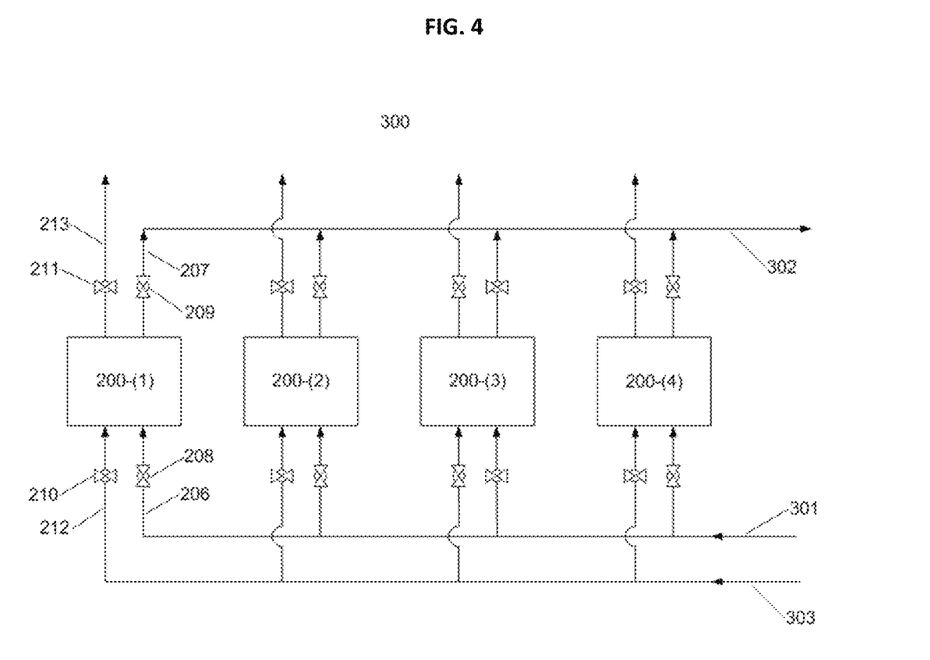
FIG. 4 is a simplified schematic diagram of the present invention in which multiple furnaces are arranged in parallel with each other.

FIG. 4 shows a simplified schematic diagram of the present invention in which multiple furnaces are arranged in parallel with each other. Multiple furnaces are arranged in parallel to form integrated furnaces 300 in FIG. 4. As an example, four furnaces (200-(1) through 200-(4)) are arranged in FIG. 4. Light alkane feed 206 to the reactors in furnaces 200 is supplied from light alkane supply 301. First merged effluent stream 207 from a furnace is further merged with each other from other furnaces to form second merged effluent stream 302. Regeneration gas feed 212 to the reactors in each of the furnaces is supplied from regeneration gas supply 303.

Each of the furnaces in FIG. 4 takes turns in an ordered manner so that the reactors in one of the furnaces transition as a group to the catalyst regenerating step. This is performed through proper operation of light alkane feed valve 208, first merged effluent valve 209, regeneration gas feed valve 210, and regeneration effluent valve 211. For example, the reactors in furnace 200-(3) of FIG. 4 transition to the catalyst regenerating step from the light alkane converting step. When the catalyst regenerating step is completed, then the reactors in furnace 200-(3) transition back to the light alkane converting step and, subsequently, reactors in one of the other furnaces in FIG. 4 transition to the catalyst regenerating step. Continuation of the ordered and harmonious transition by multiple groups of reactors realizes continuous production of aromatic hydrocarbons.

Second merged effluent stream 302 is transferred to downstream units for heat exchange and separation of liquid phase from gaseous phase. The liquid phase comprises mainly aromatic hydrocarbons. The gaseous phase consists of hydrogen, methane, and C2-C4 range alkanes and alkenes. The C2-C4 range alkanes and alkenes are recycled and mixed with the light alkane feed before being sent to the reactors for aromatic hydrocarbons production.

The invention claimed is:

1. A method for producing aromatic hydrocarbons comprising:
    contacting a light alkane with catalyst particles in at least two reactors, wherein each of the reactors is a fluidized bed reactor partially embedded in a furnace such that an upper end portion of each of the reactors is protruded from the furnace ceiling, wherein the light alkane comprises ethane, propane, butane, or a combination thereof;
    converting at least a portion of the alkane to aromatic hydrocarbons, wherein the aromatic hydrocarbons form a part of a reactor effluent stream, and wherein, during the converting step, the catalyst particles reach at least a level of a furnace ceiling inner wall;
    merging the reactor effluent streams from each of the reactors to form a first merged effluent stream; and
    regenerating the catalyst particles by either an internal-regeneration mode or an external-replacement mode, wherein the internal-regeneration mode regenerates the catalyst particles deactivated during the converting step inside the reactors and the external-replacement mode withdraws the deactivated catalyst particles from the reactors for catalyst regeneration outside the reactors and introduces catalyst particles that have sufficient activity into the reactors,
    wherein all the reactors in the furnace are transitioned as a group between the light alkane converting step and the catalyst particles regenerating step.

2. The method of claim 1, wherein the aromatic hydrocarbons comprise benzene, toluene, and xylene isomers.

3. The method of claim 1, wherein the catalyst particles are fluidized inside each of the reactors.

4. The method of claim 1, wherein the catalyst particles are 10-500 micrometers in diameter.

5. The method of claim 1, wherein, in the converting step, an outside wall of each of the reactors is heated by a flue gas, wherein the flue gas is generated by combustion of fuel.

6. The method of claim 1, wherein a pressure of the reactor is 200 prig (1480 kPa) or less during the converting step.

7. The method of claim 1, wherein a temperature of the catalyst particles is between 450° C. and 700° C. during the converting step.

8. The method of claim 1, wherein a temperature of the furnace is between 700° C. and 1200° C. during the converting step.

9. The method of claim 1, wherein the protruded portion is 10%-70% of the length of each of the reactors in a height direction.

10. The method of claim 1, wherein the furnace comprises multiple furnaces and the first merged effluent stream from each of the furnaces is further merged with each other to form a second merged effluent stream.

11. The method of claim 10, wherein the reactors are fluidly disconnected from the light alkane during the regenerating step.

12. The method of claim 10, wherein the reactors are fluidly disconnected from the second merged effluent stream during the regenerating step.

* * * * *